United States Patent
Nova et al.

(10) Patent No.: US 9,213,801 B2
(45) Date of Patent: Dec. 15, 2015

(54) MULTI-RESOLUTION GRAPHICAL DISPLAY FOR FEEDBACK ON CHEST COMPRESSION DEPTH

(75) Inventors: Richard C. Nova, Kirkland, WA (US); Robert G. Walker, Bothell, WA (US); John Carlton Daynes, Redmond, WA (US)

(73) Assignee: PHYSIO-CONTROL, INC., Redmond, WA (US)

( * ) Notice: Subject to any disclaimer, the term of this patent is extended or adjusted under 35 U.S.C. 154(b) by 919 days.

(21) Appl. No.: 13/306,883

(22) Filed: Nov. 29, 2011

(65) Prior Publication Data

US 2012/0136286 A1 May 31, 2012

Related U.S. Application Data

(60) Provisional application No. 61/417,819, filed on Nov. 29, 2010.

(51) Int. Cl.
*A61H 31/00* (2006.01)
*G06F 19/00* (2011.01)

(52) U.S. Cl.
CPC .......... *G06F 19/3406* (2013.01); *A61H 31/005* (2013.01); *A61H 31/007* (2013.01); *A61H 2201/5043* (2013.01); *A61H 2201/5064* (2013.01)

(58) Field of Classification Search
CPC .... G06F 19/3406; A61H 31/00; A61H 31/04; A61H 31/005; A61H 31/007; A61H 31/008; A61H 2201/5043; A61H 2201/5064; A61H 2201/5069; A61H 2201/5071; A61H 2203/0456
USPC .............. 601/41–44; 600/509, 515, 518, 519, 600/587, 578; 434/262–275; 607/2, 4, 5, 6, 607/59
See application file for complete search history.

(56) References Cited

U.S. PATENT DOCUMENTS 4,237,872 A * 12/1980 Harrigan ........................ 601/41
2008/0146974 A1* 6/2008 Lund et al. ...................... 601/41

FOREIGN PATENT DOCUMENTS

| EP | 1 859 770 A1 | 11/2007 |
| EP | 1 933 114 A1 | 6/2008 |
| WO | 2004/037154 A2 | 5/2004 |
| WO | 2007/033050 A2 | 3/2007 |

OTHER PUBLICATIONS

International Search Report and Written Opinion, Patent Cooperation Treaty, Aug. 10, 2012, 12 pages, PCT/US2011/062463, Rijswijk, Netherlands.

* cited by examiner

*Primary Examiner* — Quang D Thanh
(74) *Attorney, Agent, or Firm* — Marger Johnson

(57) ABSTRACT

Embodiments of the present concept are directed to medical devices. For example, a medical device including a display for providing feedback to a rescuer who is performing Cardio Pulmonary Resuscitation (CPR) chest compressions to a patient. The display is structured to graphically indicate an instantaneous value of a measured compression depth of the chest of the patient. The display includes an indicator range that corresponds at least in part to a compression depth range of some of the measured compression depths. An indicator is represented as progressing along the indicator range as the depth changes within the compression depth range to represent a value of the measured compression depth in relation to the indicator range. Depending on the measured compression depth, the indicator progresses at a variable rate relative to a difference in the measured compression depth.

20 Claims, 7 Drawing Sheets

*EXAMPLE DISPLAY IMPLEMENTATION*

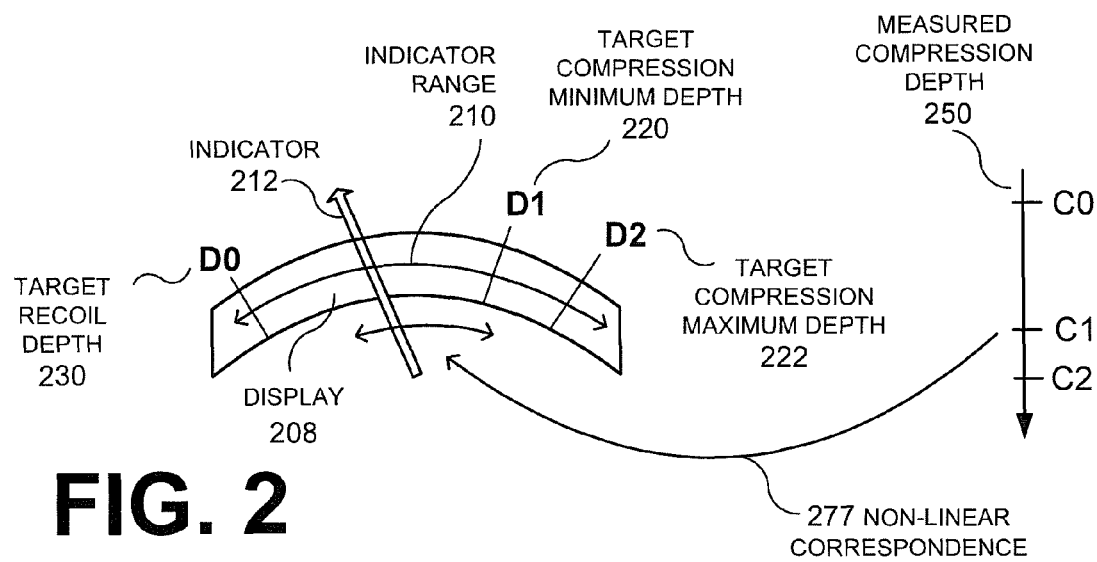
FIG. 2
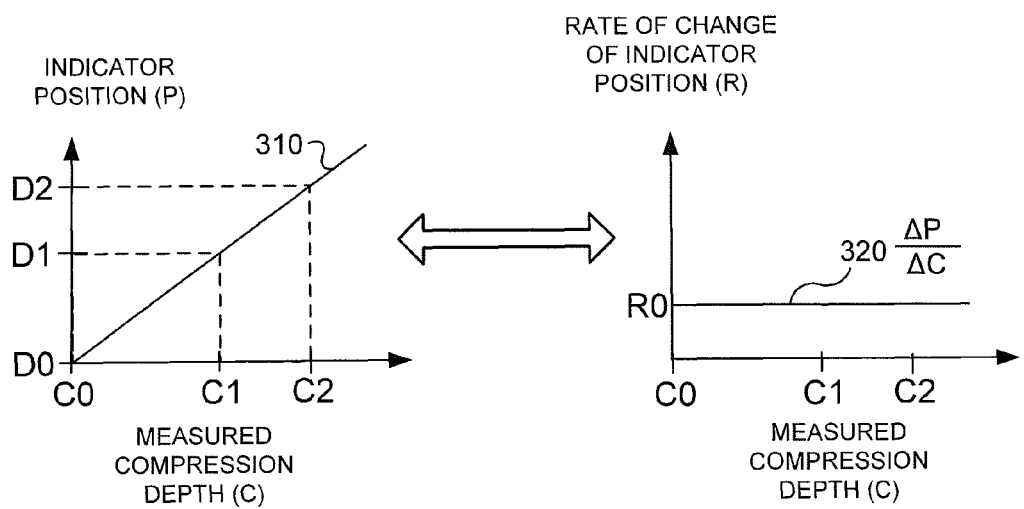
FIG. 3A
(PRIOR ART)
FIG. 3B
(PRIOR ART)

*EXAMPLE IMPLEMENTATION*

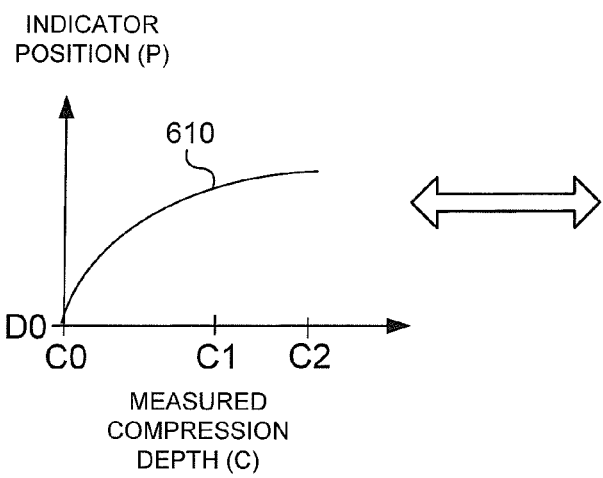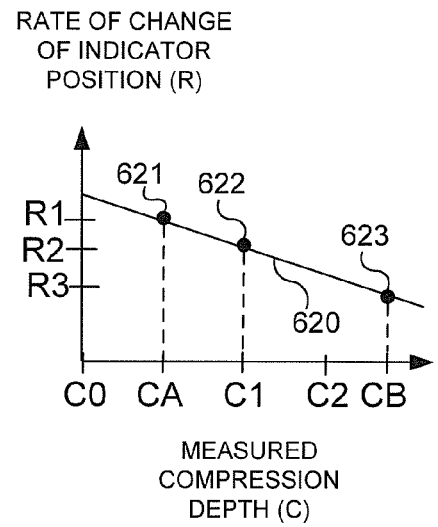
FIG. 6A  FIG. 6B
*EXAMPLE IMPLEMENTATION*
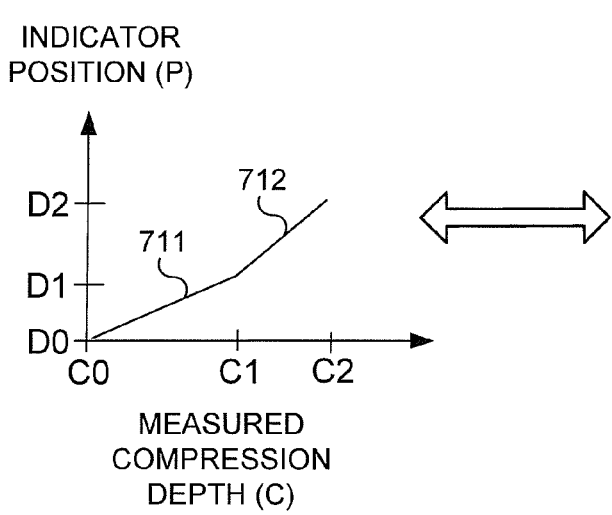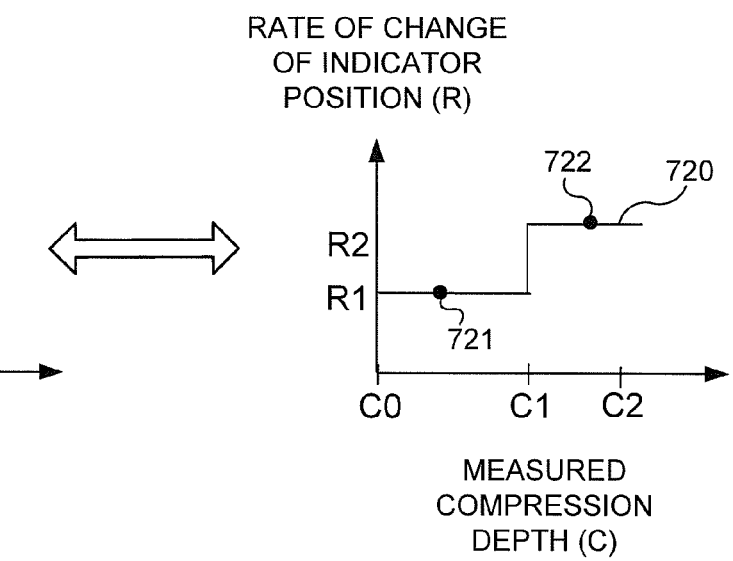
FIG. 7A  FIG. 7B
*EXAMPLE IMPLEMENTATION*

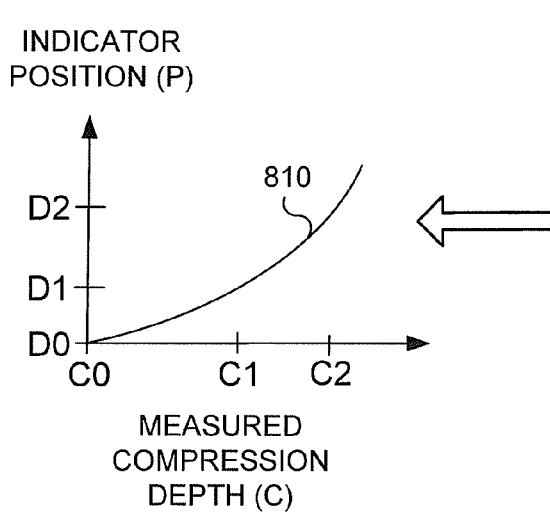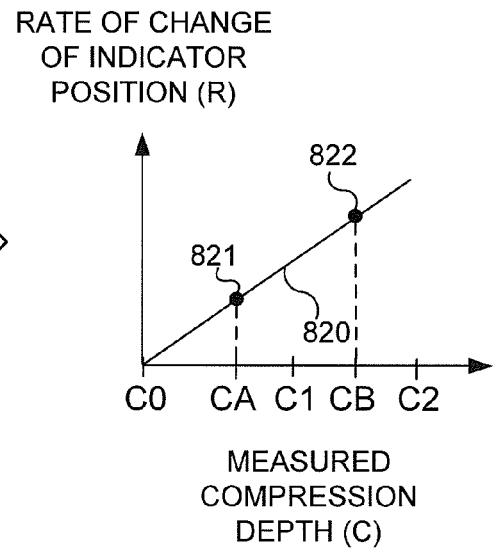
FIG. 8A
FIG. 8B
*EXAMPLE IMPLEMENTATION*
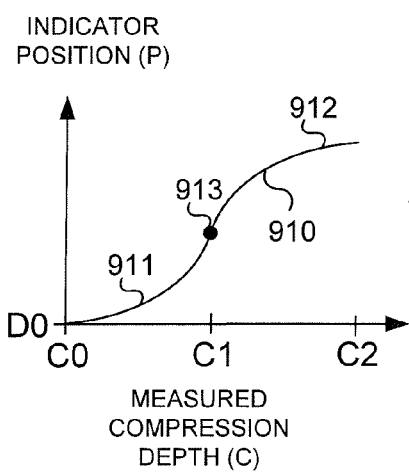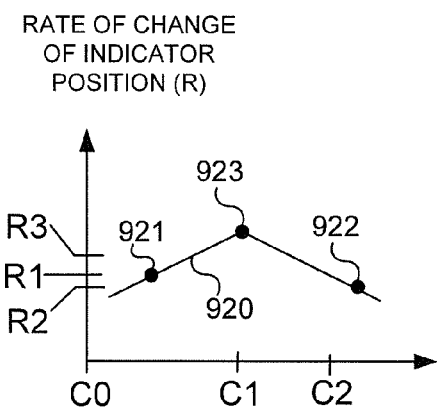
FIG. 9A
FIG. 9B
*EXAMPLE IMPLEMENTATION*

EXAMPLE DISPLAY IMPLEMENTATION

EXAMPLE DISPLAY IMPLEMENTATION

EXAMPLE DISPLAY
IMPLEMENTATION

EXAMPLE DISPLAY
IMPLEMENTATION

MULTI-RESOLUTION GRAPHICAL DISPLAY FOR FEEDBACK ON CHEST COMPRESSION DEPTH

CROSS REFERENCE TO RELATED PATENT APPLICATIONS

This patent application claims benefit from U.S. Provisional Patent Application Ser. No. 61/417,819 entitled DUAL-RESOLUTION GRAPHICAL DISPLAY FOR FEEDBACK ON CHEST COMPRESSION DEPTH, filed on Nov. 29, 2010, the disclosure of which is hereby incorporated by reference for all purposes.

FIELD

This application generally relates to medical devices.

BACKGROUND

In humans, the heart beats to sustain life. In normal operation, it pumps blood through the various parts of the body. More particularly, the various chamber of the heart contract and expand in a periodic and coordinated fashion, which causes the blood to be pumped regularly. More specifically, the right atrium sends deoxygenated blood into the right ventricle. The right ventricle pumps the blood to the lungs, where it becomes oxygenated, and from where it returns to the left atrium. The left atrium pumps the oxygenated blood to the left ventricle. The left ventricle, then, expels the blood, forcing it to circulate to the various parts of the body.

The heart chambers pump because of the heart's electrical control system. More particularly, the sinoatrial (SA) node generates an electrical impulse, which generates further electrical signals. These further signals cause the above-described contractions of the various chambers in the heart, in the correct sequence. The electrical pattern created by the sinoatrial (SA) node is called a sinus rhythm.

Sometimes, however, the electrical control system of the heart malfunctions, which can cause the heart to beat irregularly, or not at all. The cardiac rhythm is then generally called an arrhythmia. Arrhythmias may be caused by electrical activity from locations in the heart other than the SA node. Some types of arrhythmia may result in inadequate blood flow, thus reducing the amount of blood pumped to the various parts of the body. Some arrhythmias may even result in a Sudden Cardiac Arrest (SCA). In a SCA, the heart fails to pump blood effectively, and, if not treated, death can occur. In fact, it is estimated that SCA results in more than 250,000 deaths per year in the United States alone. Further, a SCA may result from a condition other than an arrhythmia.

One type of arrhythmia associated with SCA is known as Ventricular Fibrillation (VF). VF is a type of malfunction where the ventricles make rapid, uncoordinated movements, instead of the normal contractions. When that happens, the heart does not pump enough blood to deliver enough oxygen to the vital organs. The person's condition will deteriorate rapidly and, if not reversed in time, they will die soon, e.g. within ten minutes.

Ventricular Fibrillation can often be reversed using a lifesaving device called a defibrillator. A defibrillator, if applied properly, can administer an electrical shock to the heart. The shock may terminate the VF, thus giving the heart the opportunity to resume pumping blood. If VF is not terminated, the shock may be repeated, often at escalating energies.

A challenge with defibrillation is that the electrical shock must be administered very soon after the onset of VF. There is not much time: the survival rate of persons suffering from VF decreases by about 10% for each minute the administration of a defibrillation shock is delayed. After about 10 minutes the rate of survival for SCA victims averages less than 2%.

The challenge of defibrillating early after the onset of VF is being met in a number of ways. First, for some people who are considered to be at a higher risk of VF or other heart arrhythmias, an Implantable Cardioverter Defibrillator (ICD) can be implanted surgically. An ICD can monitor the person's heart, and administer an electrical shock as needed. As such, an ICD reduces the need to have the higher-risk person be monitored constantly by medical personnel.

Regardless, VF can occur unpredictably, even to a person who is not considered at risk. As such, VF can be experienced by many people who lack the benefit of ICD therapy. When VF occurs to a person who does not have an ICD, they collapse, because blood flow has stopped. They should receive therapy quickly.

For a VF victim without an ICD, a different type of defibrillator can be used, which is called an external defibrillator. External defibrillators have been made portable, so they can be brought to a potential VF victim quickly enough to revive them.

During VF, the person's condition deteriorates, because the blood is not flowing to the brain, heart, lungs, and other organs. Blood flow must be restored, if resuscitation attempts are to be successful.

Cardiopulmonary Resuscitation (CPR) is one method of forcing blood flow in a person experiencing cardiac arrest. In addition, CPR is the primary recommended treatment for some patients with some kinds of non-VF cardiac arrest, such as asystole and pulseless electrical activity (PEA). CPR is a combination of techniques that include chest compressions to force blood circulation, and rescue breathing to force respiration.

Properly administered CPR provides oxygenated blood to critical organs of a person in cardiac arrest, thereby minimizing the deterioration that would otherwise occur. As such, CPR can be beneficial for persons experiencing VF, because it slows the deterioration that would otherwise occur while a defibrillator is being retrieved. Indeed, for patients with an extended down-time, survival rates are higher if CPR is administered prior to defibrillation.

Advanced medical devices can actually coach a rescuer who performs CPR. For example, a medical device can issue instructions, and even prompts, for the rescuer to perform CPR more effectively. While basic instructions are helpful, providing feedback to the rescuer during CPR can improve the rescuer's ability to provide effective CPR. However, in order to provide effective feedback, an advanced medical device has to be able to measure various components of the administered CPR. This feedback can be difficult to provide because CPR is administered on a variety of surfaces, all with different amounts of flex or give. This surface differentiation can make compression depth measurements difficult to estimate. Embodiments of the invention address these and other deficiencies in the prior art.

BRIEF SUMMARY

The present description gives instances of medical devices, systems, and methods, the use of which may help overcome problems and limitations of the prior art.

In one embodiment, a medical device for use by a rescuer who is caring for a patient includes a mechanism for measuring a compression depth of a chest of a patient who is receiving Cardio Pulmonary Resuscitation (CPR) compressions by a rescuer. The medical device includes a display for graphically displaying an instantaneous value of the measured compression depth for providing feedback to the rescuer.

In another embodiment, a display for a medical device gives visual feedback of an instantaneous value of a measured compression depth to a rescuer who is providing Cardio Pulmonary Resuscitation (CPR) compressions to a patient. The display includes an indicator range that corresponds at least in part to a compression depth range of some of the measured compression depths. An indicator is represented as traveling along the indicator range as the depth changes within the compression depth range to indicate the instantaneous value of the measured compression depth in relation to the indicator range. For particular depths along a linear scale of measurements in the compression depth range, there are a set of corresponding depth marks on the display at non-linear scale intervals along the indicator range.

An advantage over the prior art is that the medical devices discussed in this description include features that encourage the rescuer to achieve optimal CPR compression depth for the patient during the rescue.

These and other features and advantages of this description will become more readily apparent from the following Detailed Description, which proceeds with reference to the drawings, in which:

BRIEF DESCRIPTION OF THE DRAWINGS

FIG. 2 is a conceptual diagram of how a display with an indicator has a non-linear correspondence to a measured depth according to embodiments.

FIG. 3A is a graph illustrating a linear change in indicator position relative to a change in measured depth according to the prior art.

FIG. 3B is a graph illustrating a static rate of change in indicator position relative to measured depths for the change of FIG. 3A.

FIG. 6A is a graph illustrating another example non-linear change in indicator position relative to a change in measured depth according to an embodiment of FIG. 4A.

FIG. 6B is a graph illustrating another example set of rates of change in indicator position relative to various measured depths for the change of FIG. 6A according to the embodiments.

FIG. 7A is a graph illustrating an example non-linear change in indicator position relative to a change in measured depth according to an embodiment of FIG. 4A.

FIG. 7B is a graph illustrating a sample rate of change in indicator position relative to various measured depths for the change of FIG. 7A, according to embodiments.

FIG. 8A is a graph illustrating another example non-linear change in indicator position relative to a change in measured depth according to an embodiment of FIG. 4A.

FIG. 8B is a graph illustrating another example set of rates of change in indicator position relative to various measured depths for the change of FIG. 8A according to the embodiments.

FIG. 9A is a graph illustrating another example non-linear change in indicator position relative to a change in measured depth according to an embodiment of FIG. 4A.

FIG. 9B is a graph illustrating another example set of rates of change in indicator position relative to various measured depths for the change of FIG. 9A according to the embodiments.

DETAILED DESCRIPTION

As has been mentioned, the present description is about medical devices and displays for providing feedback about to a rescuer providing care to a patient.

Embodiments are now described in more detail.

Figure 1:
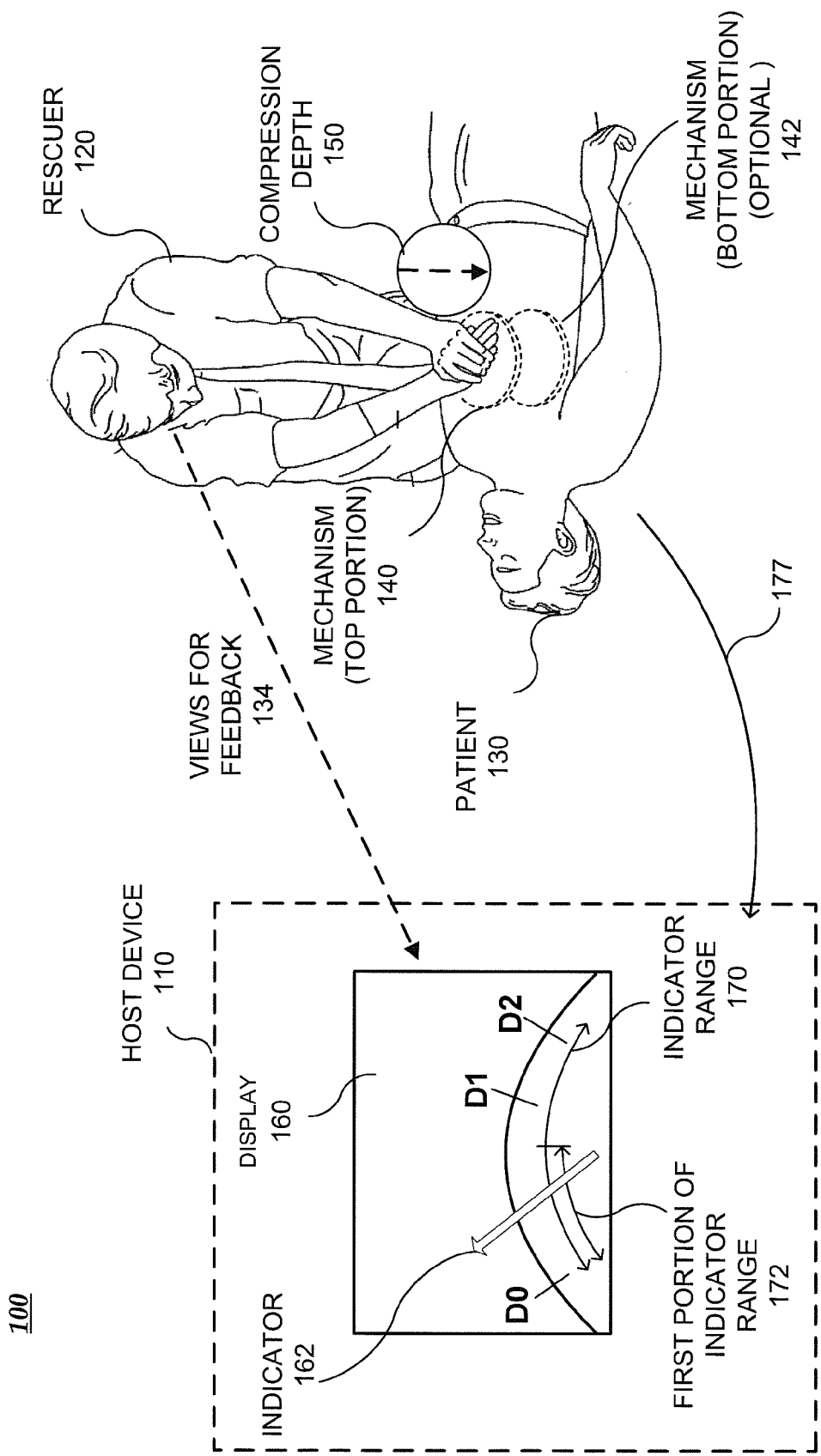
FIG. 1 is a diagram of a rescue scene including a medical device having a display that provides feedback of compression depth to a rescuer according to embodiments.

FIG. 1 is a diagram of a rescue scene including a medical device having a display that provides feedback of compression depth to a rescuer according to embodiments. A host device 110 includes a display 160 for providing feedback to a rescuer 120 who is performing Cardio Pulmonary Resuscitation (CPR) on a patient 130 experiencing cardiac arrest. An indicator 162 on the display 160 indicates to the rescuer 120 an instantaneous value of a measured compression depth of the chest of the patient 130. As the rescuer 120 compresses the chest of the patient 130, a mechanism 140 detects the depth of the compression. The mechanism may additionally include a bottom portion 142, which may lead to more accurate measurement of the depth of compression when the patient 130 is lying on a surface that yields during CPR compressions. Any mechanism 140, 142 for measuring compression depth is acceptable, such as a mechanism that uses accelerometers, gyroscopes, or compression force detectors, for example.

The measured depth, or resultant measured depth, if the bottom portion 142 is present, is provided to the host device 110, the providing of which is indicated as 177, and the instantaneous value of the measured compression depth is represented on the display 160. An indicator range 170 corresponds at least in part to a compression depth range of some of the measured compression depths 150. The indicator 162 is represented on the display 160 as progressing along the indicator range 170 as the depth changes within the compression depth range to represent a value of the measured compression depth in relation to the indicator range. In general, as the rescuer 120 performs CPR and compresses the chest of the patient 130, the indicator 162 moves to provide feedback 134 to the rescuer while the rescuer is viewing the display 160. When the measured compression depth is passing a first point of the compression depth range, the indicator 162 progresses at a first rate relative to a first difference in the measured compression depth. Then, when the measured compression depth is passing a second point of the compression depth range, which is distinct from the first point, the indicator 162 progresses at a second rate relative to the first difference in the measured compression depth. The first rate is different from the second rate.

In some embodiments the host device 110 is capable of measuring a parameter of the patient. In other embodiments the host device 110 is capable of providing a therapy to the patient. In further embodiments the host device 110 is capable of both measuring a parameter of the patient and providing a therapy to the patient. In some embodiments the host device 110 receives the representation of the instantaneous value of the measured depth from a mechanism for measuring the compression depth that is distinct from the host device, such as the mechanism 140.

FIG. 2 is a conceptual diagram of how a display with an indicator has a non-linear correspondence to a measured depth according to embodiments. A measured compression depth 250 includes points C0, C1, and C2, which correspond to different measured compression depths of the patient 130 by the rescuer 120 (FIG. 1). A display 208 includes an indicator 212 that travels along an indicator range 210 between a point D0, which is a target recoil depth indication 230 and a point D2, which is a target compression maximum depth indication 222. The target recoil depth 230, D0, is the chest depth when the rescuer fully releases downward pressure on the chest of the patient 130. The target compression maximum depth 222, D2, is the depth of the maximum recommended chest compression of the patient 130. There is also a target compression minimum depth 220 represented as point D1 on the indicator range 210. CPR is most effective when it is performed between the target recoil depth 230 and the minimum and maximum target compression depths 220, 222. In other words, during CPR, a rescuer 120 allows the chest of the patient 130 to recoil to the target recoil depth 230, then presses the chest of the patient 130 to a point between the minimum and maximum target compression depths 220, 222. This procedure is then repeated multiple times per minute, as described above, to cause blood to flow in the patient 130.

With reference to FIG. 2, as the rescuer 120 (FIG. 1) compresses the chest of the patient 130, progress of the measured chest compression is indicated as progressing along the indicator range 210 by moving the indicator 212. In this example, the indicator 212 is a line segment having a main direction substantially perpendicular to a main direction of the indicator range 210, and progressing along the indicator range is illustrated by moving the line segment along the indicator range.

By providing an instantaneous feedback of how far the chest of the patient 130 is compressed, the display 208 helps the rescuer 120 to determine the proper amount of force to press on the chest of the patient 130, and to ensure that the rescuer is completely releasing the force between presses. When the measured compression depth 250 is provided to the display 208, the indicator 212 moves along the indicator range 210 to provide feedback to the rescuer. As described below, and specifically different from the prior art, embodiments of the invention have a non-linear correspondence between the measured chest compression depth 250 and the position of the indicator 212, as indicated by reference 277 of FIG. 2.

The effect of having a non-linear correspondence in indicator position relative to a change in measured depth means that an indicator has greater or less movement at a particular measured depth. For instance, in some embodiments the device maker may want to highlight or exaggerate movement in a particular range of compression depth. For example, the indicator may move at a relatively slower rate until it reaches the target compression minimum depth 220 (FIG. 2), then move at a relatively faster rate through the target compression maximum depth 222. In some embodiments the indicator may not move at all, or move very slowly, until a particular depth has been reached, and then the indicator may move at a linear rate thereafter. Using embodiments of the invention, developers can modify or train certain behaviors in rescuers that would be difficult or impossible to achieve using conventional feedback methods.

FIG. 3A is a graph illustrating a linear change in indicator position relative to a change in measured depth according to the prior art, and FIG. 3B is a graph illustrating a static rate of change in indicator position relative to measured depths for the change of FIG. 3A. As mentioned above, in embodiments of the invention, a correspondence between the measured compression depth and the movement of indicator 212 is non-linear across the indicator range 210. This differs from behavior of the prior art, in which such correspondence is linear. For example with reference to FIG. 3A, a correspondence 310 between measured compression depth (C), shown on the x-axis and, and the indicator position (P), shown on the y-axis, is linear. Thus, in this prior art system, the indicator moves across an indicator range with direct linear correspondence to the measured depth. As illustrated in FIG. 3B, such behavior is described as having a constant rate of change of the indicator position (R) relative to a change in compression depth (C). An example constant rate 320 is illustrated in FIG. 3B as R0, and is determined by a ratio of a change of indicator position (ΔP) to a change of measured compression (ΔC).

Instead of a linear change in indicator position relative to a change in measured depth across the indicator range, as in the prior art, embodiments of the invention move the indicator, such as the indicator 212 of FIG. 2 in a non-linear manner in relation to the measured compression depth 250.

Figure 4A:
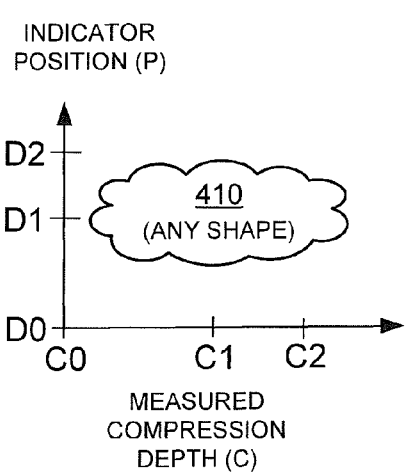
FIG. 4A is a graph illustrating a general non-linear change in indicator position relative to a change in measured depth according to embodiments.
Figure 4B:
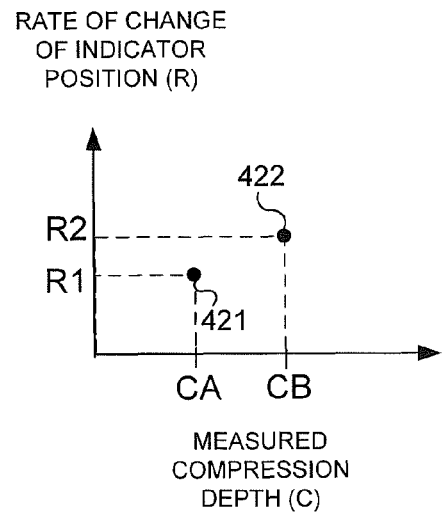
FIG. 4B is a graph illustrating only two points of a general non-static rate of change in indicator position relative to various measured depths for the change of FIG. 4A according to embodiments.
Figure 5A:
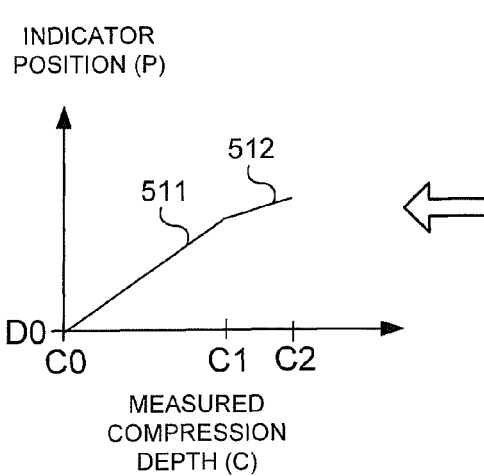
FIG. 5A is a graph illustrating an example non-linear change in indicator position relative to a change in measured depth according to an embodiment of FIG. 4A.
Figure 5B:
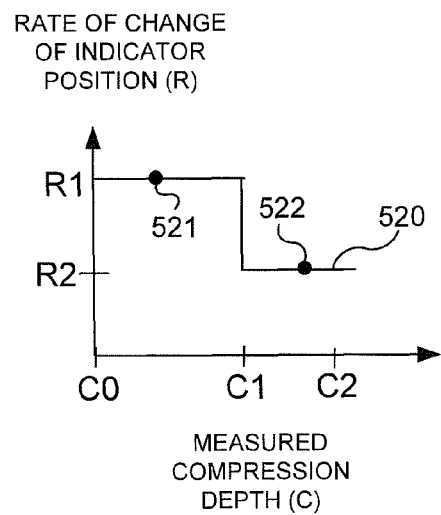
FIG. 5B is a graph illustrating a sample rate of change in indicator position relative to various measured depths for the change of FIG. 5A, according to embodiments.

FIG. 4A is a graph illustrating a general non-linear change in indicator position relative to a change in measured depth according to embodiments, and FIG. 4B is a graph illustrating only two points of a general non-static rate of change in indicator position relative to various measured depths for the change of FIG. 4A according to embodiments. According to embodiments, the correspondence between measured compression depth (C) and the indicator position (P) can be any shaped function 410. For example, with reference to FIG. 5A, the correspondence may include a first linear or approximately linear portion 511 between points C0 and C1 of measured compression depth, and then the correspondence may change to a second linear or approximately linear portion 512 between points C1 and C2 of the measured compression depth. The rate of change (R) of the indicator position for the correspondence illustrated in FIG. 5A is illustrated in FIG. 5B. In FIG. 5B, a rate of change 520 changes from a higher rate 521 for measured compression depths (C) between C0 and C1, to a lower rate 522 for measured compression depths between C1 and C2. As is illustrated in FIG. 5B, the rate 521 is different than and higher than the rate 522. Both rates 521 and 522 are non-zero rates, but in some embodiments, a rate may be zero for a portion of the measured depths. In embodiments of the invention, the points C0, C1, and C2 can correspond to any compression depths. Returning back to FIG. 4B, the rate of change of indicator position according to embodiments of the invention, can also take any shape, with the rate of change at a particular measured compression depth CA corresponding to a first rate R1, illustrated as point 421, and a second rate of change at a particular measured compression depth CB corresponding to a second rate R2, illustrated as point 422. Of course, the points 421 and 422 are just example points, and their relation in FIG. 4B is arbitrary.

FIG. 6A is a graph illustrating another example non-linear change in indicator position relative to a change in measured depth according to an embodiment of FIG. 4A, and FIG. 6B is a graph illustrating another example set of rates of change in indicator position relative to various measured depths for the change of FIG. 6A according to the embodiments. A correspondence 610 of measured compression depth (C) to indicator position (P) is illustrated in FIG. 6A. As is shown, the correspondence 610 is not a linear correspondence at any point throughout the range of the compression depth or the indicator position. Instead, as illustrated in FIG. 6B, a rate of change 620 of change in indicator position (ΔP) compared to change in measured compression depth (ΔC) is linear. For example, a rate 621 is the rate of change of indicator position when it is passing a point CA in the measured compression depth, and a rate 623 is the rate of change of indicator position when it is passing a point CB. A rate 622, between rates 621 and 623, is the rate of change of indicator position when it is passing point C1.

FIG. 7A is a graph illustrating an example non-linear change in indicator position relative to a change in measured depth according to an embodiment of FIG. 4A. FIG. 7B is a graph illustrating a sample rate of change in indicator position relative to various measured depths for the change of FIG. 7A, according to embodiments. In FIG. 7A, a correspondence portion 711, between measured compression depths C0 and C1 has a first linear region, while a second correspondence portion 712, between measured compression depths C1 and C2 has a second linear region. As can be seen in the related FIG. 7B, a rate of change of indicator position 720 has two discrete portions, 721 and 722, which correspond to rates of change of indicator position (P) R1 and R2, respectively. Also as can be seen in FIG. 7B, rate R2 is higher than rate R1. This means that an indicator, such as the indicator 212 of FIG. 2 moves at a first rate R1 during a period when the chest of the patient 130 (FIG. 1) is compressed between depths C0 and C1, and the indicator moves at a second, higher rate R2 when the chest of the patient is compressed between depths C1 and C2. This has the effect of moving the indicator 212 at a faster rate when the chest compressions are deeper.

FIG. 8A is a graph illustrating another example non-linear change in indicator position relative to a change in measured depth according to an embodiment of FIG. 4A. FIG. 8B is a graph illustrating another example set of rates of change in indicator position relative to various measured depths for the change of FIG. 8A according to the embodiments. A correspondence 810 of measured compression depth (C) to indicator position (P) is illustrated in FIG. 8A. As is shown, the correspondence 810 is not a linear correspondence at any point throughout the range of the compression depth or the indicator position. Instead, as illustrated in FIG. 8B, a rate of change 820 of change in indicator position (ΔP) compared to change in measured compression depth (ΔC) is linear. For example, a rate 821 is the rate of change of indicator position when it is passing a point CA in the measured compression depth, and a rate 823 is the rate of change of indicator position when it is passing a point CB. FIG. 8A differs from FIG. 6A in that whereas the correspondence 610 of FIG. 6A is continuously decreasing, i.e., its rate of change of indicator position 620 (FIG. 6B) is decreasing as the chest compression depth increases, the correspondence 810 of FIG. 8A is continuously increasing. This means that the indicator, such as the indicator 212 of FIG. 2 is moving along the indicator range 210 at an ever increasing rate as the chest of the patient 130 (FIG. 1) is further compressed.

FIG. 9A is a graph illustrating another example non-linear change in indicator position relative to a change in measured depth according to an embodiment of FIG. 4A. FIG. 9B is a graph illustrating another example set of rates of change in indicator position relative to various measured depths for the change of FIG. 9A according to the embodiments. A correspondence 910 of measured compression depth (C) to indicator position (P) is illustrated in FIG. 9A, and its rate of change 920 in indicator position (ΔP) compared to change in measured compression depth (ΔC) is illustrated in FIG. 9B. Differently from the correspondences 610 and 810 of FIGS. 6A and 8A, respectfully, the correspondence 910 of FIG. 9A has a portion 911 in which its rate 921 is increasing, and a second portion 912 in which its rate 922 is decreasing. Thus, the correspondence 910 includes an inflection point 913, corresponding to the point 923 in FIG. 9B, in which the rate of change 920 changes from positive to negative. The effect that such a correspondence 910 has on an indicator, such as the indicator 212 of FIG. 2 is that the indicator will move along its range 210 relatively slowly in relation to compressions at the shallow and deep portions of the measured compression depth, and will move relatively quickly during the central portions of the compressions.

Thus, with reference to FIG. 9A, if compression depth range includes points C0, C1, and C2, when the measured compression depth is passing a third point C1 of the compression depth range, that is distinct from the first point C0 and the second point C2, the indicator progresses at a third rate that is different from the first rate and the second rate relative to the first difference in the measured compression depth. In some embodiments the third rate is non-zero. In some embodiments, the third rate is one of higher and lower than the second rate and the first rate, and the third point is between the second point and the first point.

Figure 10:
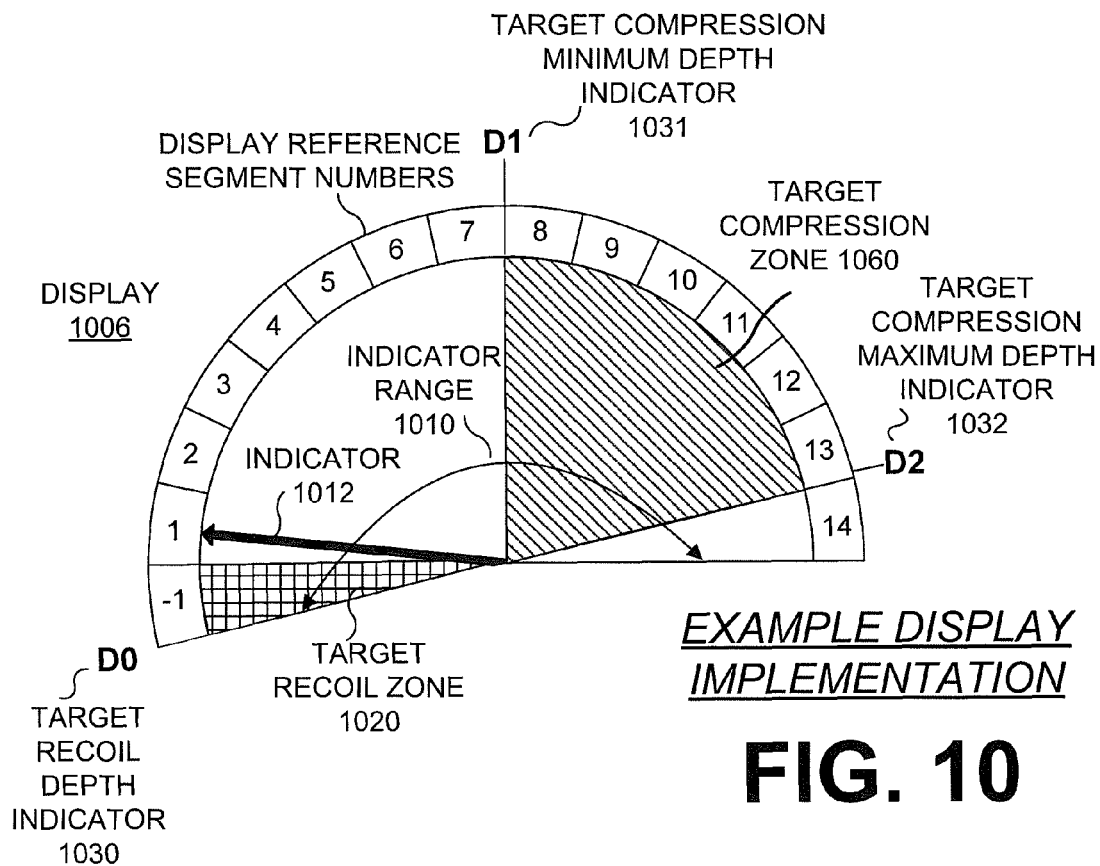
FIG. 10 is a diagram of a display having an indicator that operates according to embodiments.

FIG. 10 is a diagram of a display having an indicator that operates according to embodiments. A display 1006 includes an indicator 1012 that moves along an indicator range 1010 to provide feedback of compression depth to a rescuer 120 (FIG. 1). The indicator range 1010 includes a target compression minimum depth indicator 1031, D1 and a target compression maximum depth indicator 1032, D2. The indicator range 1010 also includes a target recoil depth indicator 1030, D0. Further the display 1006 includes two zones, a target recoil zone 1020 and a target compression zone 1060. These zones 1020, 1060 are zones in which the rescuer 120 attempts to place the indicator 1012 during the recoil and maximum depth of chest compression during CPR. Segment numbers may be used to reference or describe a position of the indicator position, for example, in training or training materials. In some embodiments only particular portions of the display 1006 may be shown. For example, during recoil, a host device 110, such as that illustrated in FIG. 1, may show the indicator 1012 and just the target recoil zone 1020, or perhaps an area just larger than the recoil zone. Then, as the rescuer 120 begins pressing on the chest of the patient 130, the host device 110 may show just the target compression zone 1060. Thus, the host device, when the measured compression depth is passing the first point in the range, may illustrate the indicator in a first view of the display, and, when the measured compression depth is passing the second point in the range, may illustrate the indicator in a second view of the display. In some embodiments, the first view and the second view have different scales of depth compression measurement.

In some embodiments, a display for a medical device is provided for giving visual feedback of an instantaneous value of a measured compression depth to a rescuer who is providing Cardio Pulmonary Resuscitation (CPR) compressions to a patient. The display may include, for example, an indicator range that corresponds at least in part to a compression depth range of some of the measured compression depths. Also, the display may include an indicator represented as traveling along the indicator range as the depth changes within the compression depth range to indicate the instantaneous value of the measured compression depth in relation to the indicator range. For particular depths along a linear scale of measurements in the compression depth range, the display also includes a set of corresponding depth marks on the display at non-linear scale intervals along the indicator range. For example, with reference to FIG. 10, a depth mark corresponding to a compression depth of zero is on the display as a target recoil depth mark, illustrated as D0. In some embodiments, depth marks correspond to compression depths of 5 cm and 6 cm are on the display, illustrated in FIG. 10 as D1 and D2. Further, a distance along the indicator range 1010 between the target recoil depth mark, D0, and the depth mark corresponding to 5 cm, D1, is approximately the same as a distance between the depth mark corresponding to 5 cm, D1, and the depth mark corresponding to 6 cm, D2. Various depth markings on displays according to embodiments of the invention may be placed based on implementation desires, and are not limitations of the invention. For example the depth markings for the display 1006 of FIG. 10 are mere examples shown here to help explain concepts of the invention.

Figure 11:
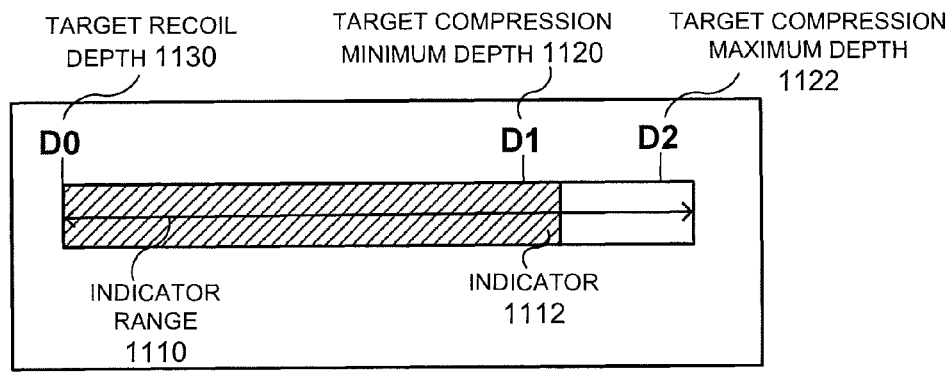
FIG. 11 is a diagram of an example display illustrating a progress bar indicator according to embodiments.

FIG. 11 is a diagram of an example display illustrating a progress bar indicator according to embodiments. An indicator range 1110 extends from a target recoil depth 1130, D0, to beyond a target compression maximum depth 1122, D2. Also illustrated is a target compression minimum depth 1120, D1. As the rescuer 120 (FIG. 1) compresses the chest of the patient 130, progress of the measured chest compression is indicated as progressing along the indicator range by extending a length of a progress bar indicator 1112.

Figure 12:
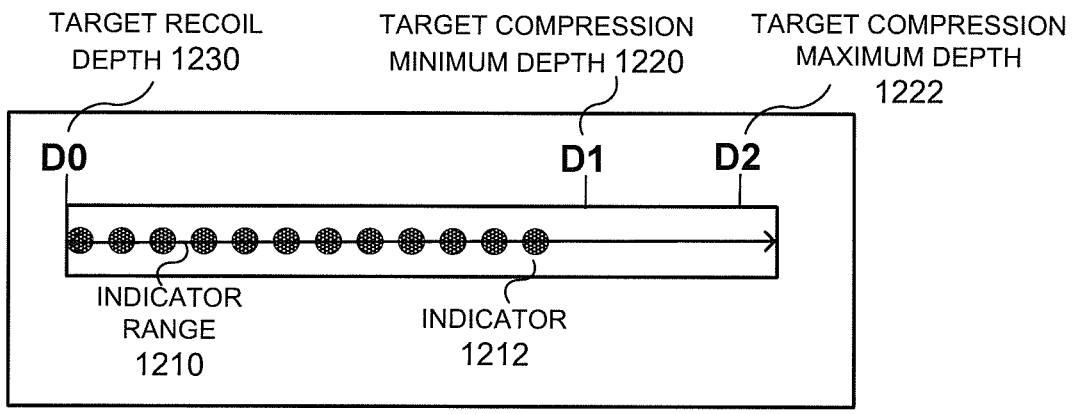
FIG. 12 is a diagram of an example display illustrating an indicator as a series of objects according to embodiments.

FIG. 12 is a diagram of an example display illustrating an indicator as a series of objects according to embodiments. An indicator range 1210 extends from a target recoil depth 1230, D0, to beyond a target compression maximum depth 1222, D2. Also illustrated is a target compression minimum depth 1220, D1. As the rescuer 120 (FIG. 1) compresses the chest of the patient 130, progress of the measured chest compression is indicated as progressing along the indicator range by adding more objects to a series of objects 1212.

Figure 13:
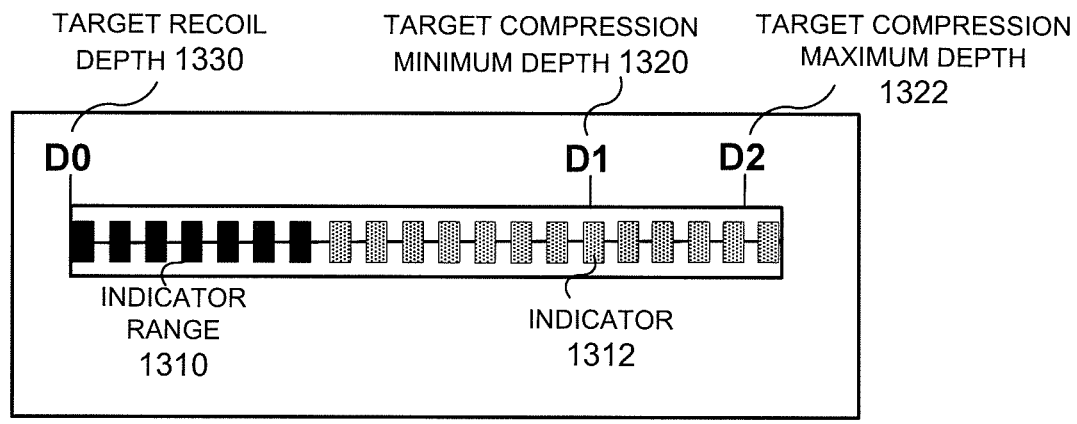
FIG. 13 is a diagram of an example display illustrating an indicator as a series of illuminated lights according to embodiments.

FIG. 13 is a diagram of an example display illustrating an indicator as a series of illuminated lights according to embodiments. An indicator range 1310 extends from a target recoil depth 1330, D0, to beyond a target compression maximum depth 1322, D2. Also illustrated is a target compression minimum depth 1320, D1. As the rescuer 120 (FIG. 1) compresses the chest of the patient 130, progress of the measured chest compression is indicated as progressing along the indicator range by illuminating more of a series of lights 1312.

In this description, numerous details have been set forth in order to provide a thorough understanding. In other instances, well-known features have not been described in detail in order to not obscure unnecessarily the description.

A person skilled in the art will be able to practice the present invention in view of this description, which is to be taken as a whole. The specific embodiments as disclosed and illustrated herein are not to be considered in a limiting sense. Indeed, it should be readily apparent to those skilled in the art that what is described herein may be modified in numerous ways. Such ways can include equivalents to what is described herein. In addition, the invention may be practiced in combination with other systems.

The following claims define certain combinations and subcombinations of elements, features, steps, and/or functions, which are regarded as novel and non-obvious. Additional claims for other combinations and subcombinations may be presented in this or a related document.

What is claimed is:

1. A medical device comprising:
   a display for providing feedback to a rescuer who is performing Cardio Pulmonary Resuscitation (CPR) chest compressions to a patient, the display structured to graphically indicate an instantaneous value of a measured compression depth of the chest of the patient, the display including:
   an indicator range that corresponds at least in part to a compression depth range of some of the measured compression depths, and
   an indicator represented as progressing along the indicator range as the depth changes within the compression depth range to represent a value of the measured compression depth in relation to the indicator range, in which:
   when the measured compression depth is passing a first point of the compression depth range, the indicator progresses at a first rate relative to a first difference in the measured compression depth, and
   when the measured compression depth is passing a second point of the compression depth range that is distinct from the first point, the indicator progresses at a second rate that is different from the first rate relative to the first difference in the measured compression depth.

2. The device of claim 1, further comprising:
   a mechanism for measuring the compression depth, and for providing the representation of the instantaneous value of a measured compression depth, and
   in which the display is coupled to a host device.

3. The device of claim 1, further comprising:
   a host device capable of one of measuring a parameter of the patient and providing a therapy to the patient, and
   in which
   the display is coupled to the host device, and
   the host device receives the representation of the instantaneous value from a mechanism for measuring the compression depth that is distinct from the host device.

4. The device of claim 1, in which
   the first rate is a rate that is approximately linear in a vicinity of the first point.

5. The device of claim 1, in which
   the indicator is a line segment having a main direction substantially perpendicular to a main direction of the indicator range, and progressing along the indicator range comprises moving the line segment along the indicator range.

6. The device of claim 1, in which
   the indicator is a progress bar, and progressing along the indicator range comprises extending a length of the progress bar.

7. The device of claim 1, in which
   the indicator is a series of objects, and progressing along the indicator range comprises adding more objects to the series of objects.

8. The device of claim 1, in which
   the indicator is a series of lights, and progressing along the indicator range comprises illuminating more of the series of lights.

9. The device of claim 1, in which
   the first rate is non-zero.

10. The device of claim 1, in which
    the second rate is higher than the first rate.

11. The device of claim 1, in which
the second rate is lower than the first rate.

12. The device of claim 1, in which
when the measured compression depth is passing a third point of the compression depth range that is distinct from the first point and the second point, the indicator progresses at a third rate that is different from the first rate and the second rate relative to the first difference in the measured compression depth.

13. The device of claim 12, in which
the third rate is non-zero.

14. The device of claim 12, in which
the third rate is one of higher and lower than the second rate and the first rate, and the third point is between the second point and the first point.

15. The device of claim 1, in which
the indicator range includes a target compression minimum depth indication and a target compression maximum depth indication.

16. The device of claim 1, in which
when the measured compression depth is passing the first point in the range, the indicator is illustrated in a first view of the display, and
when the measured compression depth is passing the second point in the range, the indicator is illustrated in a second view of the display.

17. The device of claim 16, in which
the first view and the second view have different scales of depth compression measurement.

18. A display for a medical device for giving visual feedback of an instantaneous value of a measured compression depth to a rescuer who is providing Cardio Pulmonary Resuscitation (CPR) compressions to a patient, the display comprising:
   an indicator range that corresponds at least in part to a compression depth range of some of the measured compression depths;
   an indicator represented as traveling along the indicator range as the depth changes within the compression depth range to indicate the instantaneous value of the measured compression depth in relation to the indicator range; and
   for particular depths along a linear scale of measurements in the compression depth range, a set of corresponding depth marks on the display at non-linear scale intervals along the indicator range.

19. The device of claim 18, in which a depth mark corresponding to a compression depth of zero is on the display as a target recoil depth mark.

20. The device of claim 19, in which depth marks corresponding to compression depths of 5 cm and 6 cm are on the display, and in which a distance along the indicator range between the target recoil depth mark and the depth mark corresponding to 5 cm is approximately the same as a distance between the depth mark corresponding to 5 cm and the depth mark corresponding to 6 cm.

* * * * *